United States Patent
Hiramatsu et al.

(10) Patent No.: US 7,267,802 B2
(45) Date of Patent: Sep. 11, 2007

(54) MEASUREMENT INSTRUMENT, REAGENT CARRIER USED FOR THE SAME, INFORMATION RECORDED MEDIUM, MEASUREMENT DATA CORRECTING METHOD, AND PROGRAM RECORDED MEDIUM

(75) Inventors: Hisao Hiramatsu, Kyoto (JP); Hironobu Oota, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 11/524,984

(22) Filed: Sep. 21, 2006

(65) Prior Publication Data

US 2007/0014700 A1    Jan. 18, 2007

Related U.S. Application Data

(62) Division of application No. 10/333,811, filed as application No. PCT/JP01/04515 on May 29, 2001, now Pat. No. 7,150,857.

(30) Foreign Application Priority Data

Jul. 24, 2000   (JP) ............................. 2000-222801

(51) Int. Cl.
  *B01L 3/00*   (2006.01)
  *G01N 21/00*   (2006.01)
  *G01N 31/00*   (2006.01)
  *G06F 19/00*   (2006.01)
(52) U.S. Cl. .................... 422/102; 422/67; 702/22; 702/28; 702/30; 702/32
(58) Field of Classification Search ................ 422/102
  See application file for complete search history.

(56) References Cited

U.S. PATENT DOCUMENTS 5,473,551 A * 12/1995 Sato et al. ..................... 702/19
5,719,059 A * 2/1998 Mimura et al. ............... 436/50
5,786,223 A * 7/1998 Terashima et al. ............ 436/50
6,377,896 B1   4/2002 Sato et al.
2002/0155616 A1 10/2002 Hiramatsu et al.

FOREIGN PATENT DOCUMENTS

DE    43 12 093    10/1993

(Continued)

*Primary Examiner*—Jill Warden
*Assistant Examiner*—Lore Ramillano
(74) *Attorney, Agent, or Firm*—Hamre, Schumann, Mueller & Larson, P.C.

(57) ABSTRACT

A measurement instrument for adequately correcting data in consideration of the deterioration of a reagent used for measurement over time. A deterioration correction data table where the variation of the sensitivity of each reagent from the date of manufacture of the reagent to the expiration date is recorded for each lot is stored in a deterioration correction data storage unit (3*b*). A bar code including information designating the lot and the date of manufacture is attached to the reagent. A CPU (1) designates the deterioration correction data table corresponding to the lot of the reagent used for measurement according to the reagent information read by the bar code reader of a nozzle derive unit (10), calculates the reagent sensitivity by interpolation on the measurement data with reference to the designated deterioration data table, and corrects the measurement data with respect to the deterioration of the reagent according to the calculated reagent sensitivity.

7 Claims, 6 Drawing Sheets

FOREIGN PATENT DOCUMENTS

| | | |
|---|---|---|
| EP | 0 562 425 | 9/1993 |
| JP | 4-128657 | 4/1992 |
| JP | 8-15265 | 1/1996 |
| JP | 9-127122 | 5/1997 |
| JP | 9127122 A * | 5/1997 |
| JP | 9-325150 | 12/1997 |
| JP | 10-213546 | 8/1998 |
| JP | 11-194108 | 7/1999 |

* cited by examiner

MEASUREMENT INSTRUMENT, REAGENT CARRIER USED FOR THE SAME, INFORMATION RECORDED MEDIUM, MEASUREMENT DATA CORRECTING METHOD, AND PROGRAM RECORDED MEDIUM

CROSS REFERENCE TO RELATED APPLICATIONS

This application is a Division of application Ser. No. 10/333,811, filed Jan. 23, 2003 now U.S. Pat. No. 7,150,857, which is a National Stage of Application No. PCT/JP01/04515, filed May 29, 2001, which applications are incorporated herein by reference.

TECHNICAL FIELD

The present invention relates to a measurement instrument and a measurement method for measuring a specific component in a body fluid (specimen) such as blood, urine, etc. by using a reagent cartridge in which a liquid reagent is filled in advance, a test piece, and the like. More specifically, the present invention relates to a measurement instrument and a measurement method for adequately correcting data in accordance with the deterioration of a reagent over time.

BACKGROUND ART

Conventionally, in particular, in the field of the clinical examination, a known measurement instrument includes a measurement instrument for reacting a specimen such as human blood, urine, etc., with a reagent, and measuring, for example, the change of the absorbance of the reagent, thereby determining a specific component in the specimen.

As such a conventional measurement instrument, an instrument using a disposable reagent is known. The disposable reagent can be classified into a cartridge type reagent in which a liquid reagent is filled in a container (hereinafter, "a reagent cartridge" will be referred to) and a test piece, that is, a so-called dry reagent.

The test piece is allowed to carry a reagent by impregnating a filter paper or sheet resin, etc., or by forming a reagent layer on a base material. Before reacting with a specimen, the test piece is in a dry state or in a substantially dry state (at least not in a liquid state). That's why the test piece is referred to as a dry reagent.

On the other hand, the reagent cartridge, which has a plurality of chambers into which necessary reagents, etc. are dispensed in accordance with items to be measured, is supplied in a state in which it is sealed by measurement instrument makers, reagent makers, etc. At the time of measurement, when a specimen is filled in a specimen chamber of the reagent cartridge and then the reagent cartridge is set in the measurement instrument, the measurement instrument, for example, automatically mixes the specimen with the reagent, and carries out the measurement.

A conventional measurement instrument corrects the reagent sensitivity before measurement by taking the deterioration of a reagent over time and a difference of a reagent between lots into account. That is, every time a user of the measurement instrument purchases a new lot of reagent cartridge or test piece, the user carries out the work including measuring a material having a known concentration by using the purchased reagent cartridge or the test piece, thereby forming a calibration curve for each lot of the reagent cartridge or the test piece, and storing it in the instrument.

In general, the user carries out a measurement of two kinds of materials, that is, a high concentration standard liquid and a low concentration standard liquid, forms a calibration curve as a linear expression by connecting both measurement values, and stores the formed calibration curve in a recording medium such as a magnetic card that can be read by the measurement instrument. This work takes a lot of time and labor. Therefore, in many cases, makers of a reagent cartridge or test piece manufacture a recording medium in which information of a calibration curve is stored for each lot and ship the above-mentioned recording medium together with the reagent cartridge or the test piece by attaching it on the reagent cartridge or the test piece.

However, as mentioned above, since the conventional measurement instrument carries out the linear expression correction by a calibration curve, there have been problems in that it is difficult to carry out an adequate correction in accordance with the difference between lots of a reagent, and that in the case where the reagent sensitivity in accordance with the deterioration over time changes non-linearly, an adequate correction cannot be carried out.

DISCLOSURE OF THE INVENTION

In order to solve these problems, it is an object of the present invention to provide a measurement instrument for adequately correcting data in accordance with the difference between lots and the deterioration of a reagent over time used for measurement.

In order to achieve the above-mentioned object, the measurement instrument of the present invention carries out a measurement by using a reagent carrier that carries a reagent in accordance with items to be measured, and carries out a deterioration correction of the measurement data in accordance with the deterioration of the reagent used for measurement over time. To the reagent carrier, an information indicator, in which reagent information including information necessary to designate the lot and the date of manufacture is recorded, is attached. The measurement instrument includes a deterioration correction data storage unit for storing a deterioration correction data table showing the situation of the deterioration over time from the date of manufacture to the expiration date by the deterioration indices at plural points on a time series for each lot of the reagent carrier; an indicator reading unit for reading the reagent information from the information indicator attached to the reagent carrier to be measured; a measurement date obtaining unit for obtaining the measurement date when the measurement is executed; and a measurement controlling unit for designating the deterioration correction data table corresponding to the lot of the reagent carrier to be measured with reference to the deterioration correction data storage unit based on the reagent information read by the indicator reading unit, calculating a deterioration index by interpolation at the measurement date based on the deterioration indices at the preceding point and the following point of the measurement date among deterioration indices recorded in the designated deterioration correction data table, and carrying out the deterioration correction of the measurement data based on the calculated deterioration index.

According to this configuration, the deterioration correction data table is stored in the deterioration correction data storage unit. The deterioration correction data table shows the situation of the deterioration over time from the date of manufacture to the expiration date as the deterioration indices at plural points on a time series for each lot of the reagent carrier. The information reading unit reads out the reagent information including the information necessary to designate the lot and the date of manufacture of the reagent carrier. The measurement controlling unit designates the deterioration correction data table corresponding to the lot of the reagent carrier used for measurement. Note here that as the deterioration index in the deterioration correction data table, for example, the numerically represented reagent sensitivity can be used.

Furthermore, the measurement controlling unit designates two consecutive points corresponding to the preceding point and the following point of the measurement date among the deterioration indices at plural points recorded on a time series, calculates the deterioration index at the measurement date by interpolation from the deterioration indices at these two points, and carries out the deterioration correction of the measurement data based on the calculated deterioration index.

Thus, even if the deterioration index over time changes non-linearly, it is possible to calculate the deterioration index of a reagent at the measurement date exactly. Furthermore, since the deterioration correction data table is provided for each lot of the reagent carrier, it is possible to solve the difference of the reagent sensitivities, etc. between lots. As a result, it is possible to provide a measurement instrument capable of obtaining the measurement data adequately corrected in accordance with the deterioration over time and the difference between lots of a reagent without the need for the calibration before measurement.

In the above-mentioned measurement instrument, it is preferable that the measurement controlling unit derives a deterioration index calculation expression that satisfies the deterioration indices at two points based on an earlier point of the two points, calculates the number of days from the earlier point of the two points to the measurement date, and substitutes the number of days in the deterioration index calculation expression, thereby calculating the deterioration index at the measurement date. Thus, it is possible to calculate the deterioration index at the measurement date exactly.

In the measurement instrument with preferred configuration, it is preferable that the deterioration index calculation expression is a linear expression. Thus, it is possible to derive the deterioration index calculation expression by a simple calculation.

It is preferable that the measurement instrument further includes an information reading unit for reading information from an information recorded medium, using the information recorded medium in which the deterioration information representing the situation of the deterioration over time from the date of manufacture to the expiration date for each lot of the reagent carrier, reading the deterioration information from the information recorded medium by the information reading unit, forming the deterioration correction data table based on the read deterioration information, and storing it in the deterioration correction data storage unit.

According to this configuration, with a simple operation of allowing the information recording unit to read the information recorded medium, the deterioration correction data table of the reagent carrier used for measurement can be stored in the deterioration correction data storage unit. Note here that this information recorded medium can be supplied to a user of the measurement instrument in a way in which, for example, a maker etc. of a reagent carrier, at the time of manufacture, forms the information recorded medium for each lot of the reagent carrier and attaches it on the manufactured reagent carrier and ships the information recorded medium together with the measurement carrier.

In the measurement instrument, the deterioration information recorded in the information recorded medium is a differential data table showing the difference between the deterioration index at each point and the deterioration index at the preceding point of the point with respect to plural points from the date of manufacture to the expiration date. Thus, as compared with the case where the deterioration correction data table itself is recorded as the deterioration information, it is advantageous that the volume of the deterioration information to be recorded in the information recorded medium may be small.

In the measurement instrument, it is further preferable that the deterioration information recorded in the information recorded medium is the deterioration correction data table. Thus, it is possible to store the deterioration correction data table in the measurement instrument by a simple process of copying the deterioration information that is recorded in the information recorded medium in the deterioration correction data storage unit.

In the measurement instrument, it is preferable that plural points in the deterioration correction data table are at equal time intervals.

In the measurement instrument, it is preferable that the larger the changing rate of the deterioration index is, the shorter the time intervals of the plural points in the deterioration correction data table are, and the smaller the changing rate of the deterioration index is, the longer the time intervals of the plural points in the deterioration correction data table are. According to this configuration, in the case where the deterioration index changes non-linearly, it is possible to calculate the deterioration index at the measurement date exactly.

In the measurement instrument, it is preferable that a reagent cartridge formed by filling a liquid reagent in accordance with the items to be measured in a container and sealing the container or a test piece is used as the reagent carrier.

In order to achieve the above-mentioned object, the first reagent carrier of the present invention is used for the above-mentioned measurement instrument and is a reagent cartridge formed by filling a liquid reagent in accordance with the items to be measured in a container and sealing the container. To the reagent cartridge, an information indicator, in which reagent information necessary to designate the lot and the date of manufacture is recorded, is attached.

Furthermore, the second reagent carrier of the present invention is a test piece to which an information indicator, in which reagent information including information necessary to designate the lot and the date of manufacture, is attached.

According to these reagent carriers, since the lot information of the reagent carrier is read out from the reagent information indicator of the reagent carrier, a user of the measurement instrument is not required to carry out operations for inputting the lot information in the measurement instrument.

In the first or the second reagent carrier, it is preferable that the information indicator is an indicator that can be read out optically.

In order to achieve the above-mentioned object, the first information recorded medium of the present invention is used for measurement instrument. In the first information recorded medium, as the deterioration information of each lot of the reagent information carrier, a differential data table showing the difference between the deterioration index at each point and the deterioration index at the preceding point of the point with respect to plural points from the date of manufacture to the expiration date is recorded.

Thus, as compared with the case where the deterioration correction data table itself is recorded as the deterioration information, it is advantageous that the volume of the deterioration information to be recorded in the information recorded medium may be small.

In order to achieve the above-mentioned object, the second information recorded medium of the present invention is used. In the second information recorded medium, as the deterioration information of each lot of the reagent carrier, the deterioration correction date table itself is recorded.

Thus, since the measurement instrument may copy the deterioration correction data table recorded in the information recorded medium in the deterioration correction data storage unit, it is advantageous that the processing block, etc. for forming the deterioration correction data table is not necessary.

It is preferable that the above-mentioned information recorded medium is any one of a magnetically recorded medium in which the deterioration information is a magnetically recorded, a magneto-optically recorded medium in which the deterioration information is magneto-optically recorded, and the deterioration information is recorded in a state in which it can be read out optically.

Furthermore, in order to achieve the above mentioned object, a method of the present invention corrects measurement data for carrying out a correction in accordance with the deterioration of a reagent over time with respect to the measurement data measured by using a reagent carrier that carries a reagent in accordance with items to be measured. To the reagent carrier, an information indicator, in which reagent information including information necessary to designate the lot and the date of manufacture is recorded, is attached. The method includes: designating a deterioration correction data table corresponding to the lot of the reagent carrier used for measurement in the deterioration correction data table showing the situation of the deterioration of a reagent over time from the date of manufacture to the expiration date by the deterioration indices at plural points on a time series for each lot of the reagent carrier based on the reagent information obtained from the information indicator of the reagent carrier used for measurement, extracting the deterioration indices at the preceding point and the following point of the measurement date of the measurement data in the deterioration indices recorded in the designated deterioration correction data table, calculating the deterioration index by interpolation at the measurement date based on the deterioration indices at the two extracted points, and carrying out the deterioration correction of the measurement data based on the calculated deterioration index.

According to this method, by referring to the deterioration correction data table in which the situation of the deterioration of a reagent over time from the date of manufacture to the expiration date is shown on a time series by the deterioration indices at plural times, the deterioration index at measurement time by interpolation from the deterioration indices at two consecutive points corresponding to the preceding and the following points of the measurement date. Based on the calculated deterioration indices, the deterioration of the measurement date is corrected.

Thus, even if the deterioration index over time changes curvedly, it is possible to calculate the deterioration index of the reagent at the measurement date exactly. Furthermore, since the deterioration correction data table is provided for each lot of the reagent carrier, it is possible to solve the difference of the reagent sensitivity, etc. between lots. As a result, it is possible to obtain adequately corrected measurement data in accordance with the deterioration over time and the difference between lots of the reagent without the need for the calibration before measurement.

In the above-mentioned method for measuring data, it is preferable that the process of calculating the deterioration index by interpolation at the measurement date includes: deriving the deterioration index calculation expression, which satisfies the deterioration indices at the two points based on an earlier point of the two points, calculating the number of days from the earlier point of the two points to the measurement date, and substituting the number of days into the deterioration index calculation expression, thereby calculating the deterioration index at the measurement date.

Thus, it is possible to calculate the deterioration index at the measurement date by using the deterioration index calculation expression approximately showing the change of the deterioration index for a relatively short time including the measurement date.

Furthermore, it is preferable that the deterioration index calculation expression is a linear expression. Thus, it is possible to derive the deterioration index calculation expression by a simple calculation.

In the method for correcting the measurement data, it is preferable that an information recorded medium in which the deterioration information representing the situation of the deterioration of a reagent over time from the date of manufacture to the expiration date for each lot is formed, and before measurement, the deterioration information is read from the information recorded medium, and the deterioration correction data table is formed based on the read deterioration information.

Thus, information necessary to form the deterioration correction data table for each lot of the reagent carrier is available via the information recorded medium from, for example a maker, etc. of a reagent carrier via the information recorded medium.

Furthermore, in order to achieve the above-mentioned object, according to the program recorded medium of the present invention, a program for controlling the operation for carrying out the deterioration correction of the measurement data in accordance with the deterioration over time of a reagent used for measurement in a measurement instrument for carrying out a measurement by using a reagent carrier that carries a reagent in accordance with items to be measured is recorded. To the reagent carrier, an information indicator, in which a reagent information including information necessary to designate the lot and the date of manufacture is recorded, is attached. The program includes designating a deterioration correction data table corresponding to the lot of the reagent carrier used for measurement by referring to the deterioration correction data table storage unit storing the deterioration correction data table showing the situation of the deterioration of a reagent over time from the date of manufacture to the expiration date for each lot of the reagent carrier as the deterioration indices at plural points on a time series based on the reagent information obtained from the information indicator of the reagent carrier used for measurement, extracting the deterioration indices at the preceding point and the following point of the measurement date of the measurement data in the deterioration indices recorded in the designated deterioration correction data table, calculating the deterioration index by interpolation at the measurement date based on the deterioration indices at the two extracted points, and executing a correction calculation of the measurement data based on the calculated deterioration index.

Thus, it is possible to realize the measurement instrument capable of appropriately carrying out the deterioration correction of the measurement data in accordance with the deterioration of the reagent used for measurement over time and the difference between the lots by allowing the CPU etc. to execute the recorded program.

In the above-mentioned program recorded medium, it is preferable that the process of calculating the deterioration index by interpolation at the measurement date includes: deriving a deterioration index calculation expression, which satisfies the deterioration indices at the two points based on an earlier point of the two points, calculating the number of days from the earlier point of the two points to the measurement date, and substituting the number of days into the deterioration index calculation expression, thereby calculating the deterioration index at the measurement date.

Thus, it is possible to calculate the deterioration index at the measurement date by using the deterioration calculating expression for representing the change of the deterioration index for a relatively short time including the measurement date approximately.

Furthermore, it is preferable that the deterioration index calculation expression is a linear expression. Thus, it is possible to derive the deterioration index calculation expression by a simple calculation.

BEST MODE OF CARRYING OUT THE INVENTION

Hereinafter, one embodiment of the present invention will be explained with reference to the drawings.

The measurement instrument according to this embodiment uses a reagent cartridge (reagent carrier) in which liquid reagent, etc. necessary for measurement was dispensed in advance. The measurement instrument, after the reagent cartridge in which a specimen such as human blood, urine, etc. is filled is provided, carries out all the operations necessary for measurement in the reagent cartridge so as to form a test sample. The operations include, for example, diluting the specimen, stirring/mixing the specimen and the reagent, and the like. Then, the obtained test sample transmits light with a predetermined wavelength and the light absorption (absorbance) is measured. Thus, a simple measurement is carried out.

Firstly, the reagent cartridge used in the measurement instrument will be explained.

Figure 2:
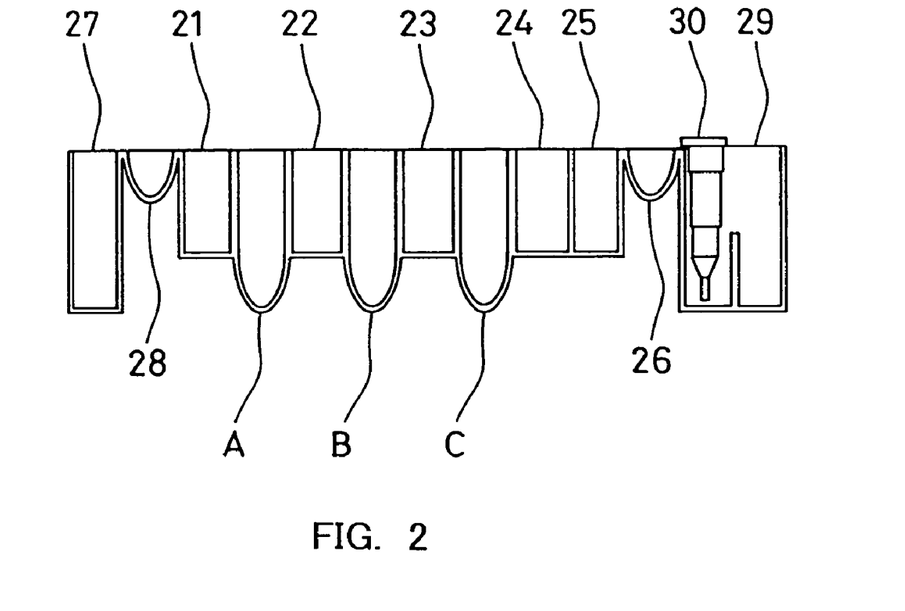
FIG. 2 is a cross-sectional view showing a configuration of a reagent cartridge as one example of a reagent carrier used at the time of measurement with the measurement instrument.
Figure 3:
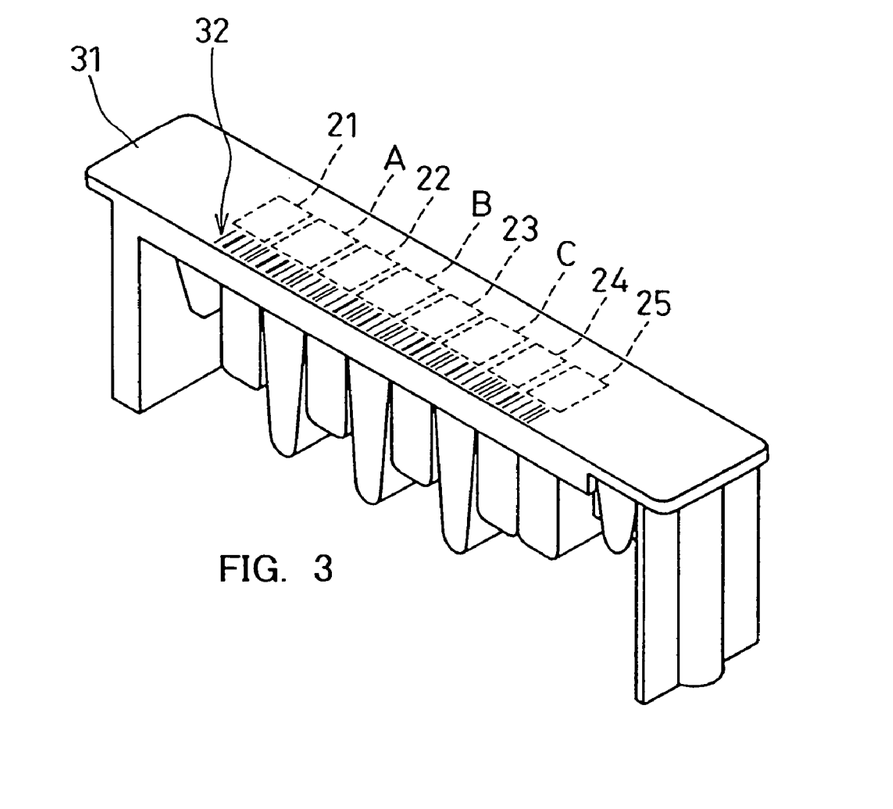
FIG. 3 is a perspective view showing a configuration of the reagent cartridge shown in FIG. 2.

FIG. 2 is a cross-sectional view and FIG. 3 is a perspective view, respectively showing the configuration of a reagent cartridge used in the measurement instrument. As shown in FIG. 2, the reagent cartridge used in the measurement instrument includes a plurality of wells 21 to 26, a plurality of cells A to C, a specimen container holder 27, a specimen chamber 28, and a waste chamber 29.

A material for the container part of the reagent cartridge is not particularly limited except that a transparent material is used for at least a part that transmits light when the absorbance is measured. However, it is preferable to use, for example, polystyrene resin etc. from the viewpoint of production management and cost.

In the specimen chamber 28, in preparation for measurement, a specimen is filled in by a pipet etc. In the specimen container holder 27, a specimen necessary to be centrifuged that is filled and centrifuged can be set. In the specimen chamber 28, a specimen that is not necessary to be centrifuged (for example, whole blood, etc.) also can be filled and measured.

The waste chamber 29 is a chamber in which a waste liquid is stored, but when the reagent cartridge is shipped, a tip 30 used at the time of measurement is accommodated therein. The tip 30 is removed from the waste chamber 29 in preparation for measurement and is attached to the tip of a nozzle (mentioned below) of the measurement instrument. The tip 30 has a function of sucking/draining a specimen, reagent, and the like, by the operation of a sampling pump unit (mentioned below) of the measurement instrument.

In the wells 21 to 26 and the cells A to C, a liquid reagent, a dilution solution and a washing solution, etc. are dispensed in accordance with the items to be measured. Note here that in the reagent cartridge, as shown in FIG. 3, a reagent etc. in accordance with the items to be measured is filled in the wells or the cells in advance so that the measurement can be carried out with respect to the specific items to be measured, and thereafter the reagent cartridge is sealed by attaching a seal 31 on the upper surface of a pack.

Furthermore, on the surface of the seal 31, a bar code 32 is attached to the side of the open parts of the wells 21 to 26 and the cells A to C. The bar code 32 includes information such as the item number to be measured, the reagent cartridge number, the lot number, the date of manufacture, the expiration date, and the like, as the information concerning the reagent cartridge (reagent information). Note here the bar code 32 may include information other than the above as long as it is within the range of the amount that can be recorded in the bar code 32.

Next, a configuration of the measurement instrument according to the embodiment will be explained.

Figure 1:
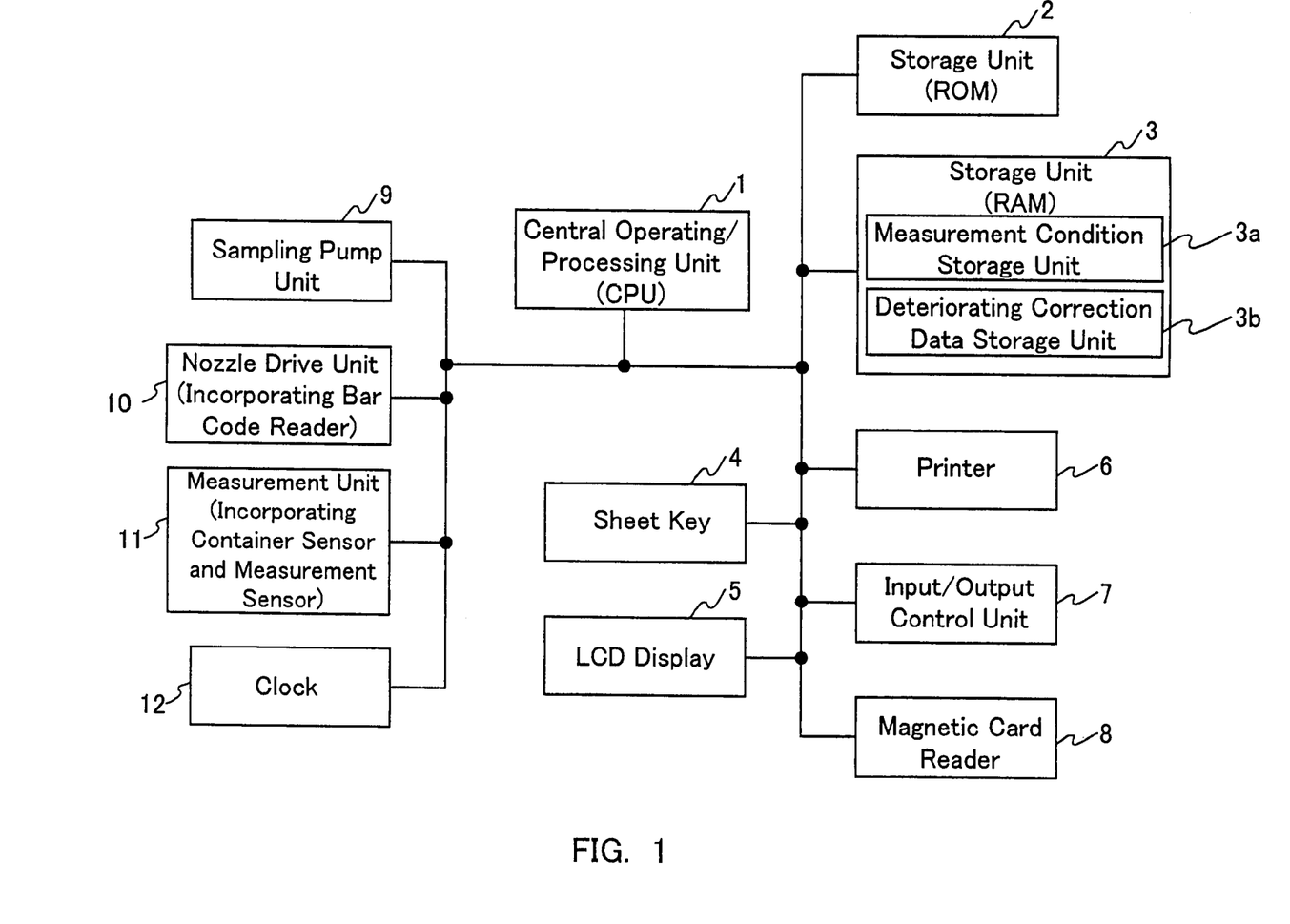
FIG. 1 is a block diagram showing a configuration of a measurement instrument according to one embodiment of the present invention.

FIG. 1 is a block diagram showing a configuration of the measurement instrument. The measurement instrument includes a central calculating/processing unit (CPU) 1, a ROM 2, a RAM 3, a sheet key 4 for a user to input operation indication, etc., an LCD display 5 made of liquid crystal display, a printer 6 for printing out measurement results, etc., an input/output control unit 7 realized by a communication interface, for example, RS-232C, etc., a magnetic card reader 8 (information reading unit), a sampling pump unit 9, a nozzle drive unit 10, a measurement unit 11, and a clock 12 (a measurement date obtaining unit) for obtaining the measurement time.

In the ROM 2, a program etc. for controlling the operation of the measurement instrument is stored. An example of the stored program includes, for example, a measurement controlling program for controlling the measurement operation of the measurement instrument, a deterioration correction date registering program for registering the deterioration correction data in the measurement instrument, and a deterioration correction calculating program for carrying out the correction in accordance with the deterioration of a reagent over time with respect to the measured data (deterioration correction), and the like.

The RAM 3 includes a measurement conditions storage unit 3a for storing various conditions concerning the measurement for each item to be measured, and a deterioration correction data storage unit 3b for storing the deterioration correction data table, etc. of the reagent cartridge used in the measurement instrument. The correction deterioration data table numerically represents the reagent sensitivity for a manufacturing lot of the reagent cartridge used for each item to be measured every time a predetermined term (for example, one month) has passed since the lots were manufactured.

Note here that the data of the deterioration correction data table are supplied by a maker etc. of reagent cartridges. For example, a maker of reagent cartridges forms data representing the change over time of the reagent sensitivity for each lot of the reagent cartridge; records the data in a magnetic card; attaches the magnetic card on the reagent cartridge; and then ships the reagent cartridge. A user of the measurement instrument can register the deterioration correction data table about a newly purchased reagent cartridge in the RAM 3 by allowing the magnetic card reader 8 to read the data recorded in the magnetic card attached to the purchased reagent cartridge. This registering process of this deterioration correction data table will be explained in detail later.

The sampling pump unit 9 includes a pump and controls the sucking and draining of a specimen, a reagent, and the like, via the tip 30 attached to the tip part of the nozzle of the nozzle drive unit 10 by the operation of this pump under the control of the CPU 1. The nozzle drive unit 10 controls the operation of the nozzle on the reagent cartridge under the control of the CPU 1.

The nozzle of the nozzle drive unit 10 also functions for opening the seal 31 of the reagent cartridge when the reagent cartridge is set in the measurement instrument and the measurement starts. This nozzle is formed of, for example, stainless steel, etc. and can perforate the seal 31. The nozzle drive unit 10 perforates the seal 31 at the open part such as wells, cells, and the like, necessary for measurement like this; then inserts the nozzle tip part into the tip 30 loaded in the waste chamber 29; and pulls it out so as to attach the tip 30 to the nozzle.

The CPU 1, for example, transfers the reagent etc. dispensed in the reagent cartridge to the other wells or cells by controlling the operation of the sampling pump unit 9 and the nozzle drive unit 10 as mentioned below.

Firstly, the CPU 1 shifts the nozzle of the nozzle drive unit 10 horizontally along the upper surface of the reagent cartridge, and then temporarily stops it on the target well or cell. Subsequently by dropping the nozzle into the well or cell, the tip part of the tip 30 attached to the nozzle tip part is allowed to reach a liquid surface of the well or cell, and thereafter the sampling pump unit 9 is allowed to carry out the sucking operation, thus allowing the reagent etc. dispensed in the well or cell to be sucked in the tip 30.

Furthermore, by raising the nozzle from the well or cell, horizontally shifting the nozzle to the other well or cell, dropping the nozzle into the well or cell, and then allowing the sampling pump unit 9 to carry out the draining operation. Thus, reagent etc. of one well or cell is transferred to the other well or cell.

Furthermore, a washing solution is dispensed in any one of wells and the operation of sucking the washing solution from the well to the tip 30 and draining into the waste chamber 29 is repeated, and thereby the tip 30 can be washed and unnecessary reagent, etc. can be prevented from mixing.

In the measurement instrument, the CPU 1 controls the operation of the sampling pump unit 9 and the nozzle drive unit 10 and transfers a predetermined amount of specimens, reagent or diluted solution, etc. from one well or cell to the other well or cell in accordance with the predetermined procedure corresponding to the items to be measured, thereby diluting the specimen or mixing it with a reagent and forming the measurement test sample. In the measurement condition storage unit 3a of the RAM 3, the operation procedures in accordance with the items to be measured of the sampling pump unit 9 and the nozzle drive unit 10 are stored. The CPU 1 refers to them when the measurement is executed.

Furthermore, the nozzle drive unit 10 includes a bar code reader (indicator reading unit) for reading out the bar code 32 of the reagent cartridge. The measurement unit 11 includes a mechanism for fixing the reagent cartridge as well as a container sensor for distinguishing whether or not the reagent cartridge is set in the mechanism and a measurement sensor. Note here that as the measurement sensor, it is possible to use a spectrophotometer etc. for measuring the absorbance of the test sample by using light with a predetermined wavelength.

Next, the operation of the measurement instrument will be explained.

Figure 4:
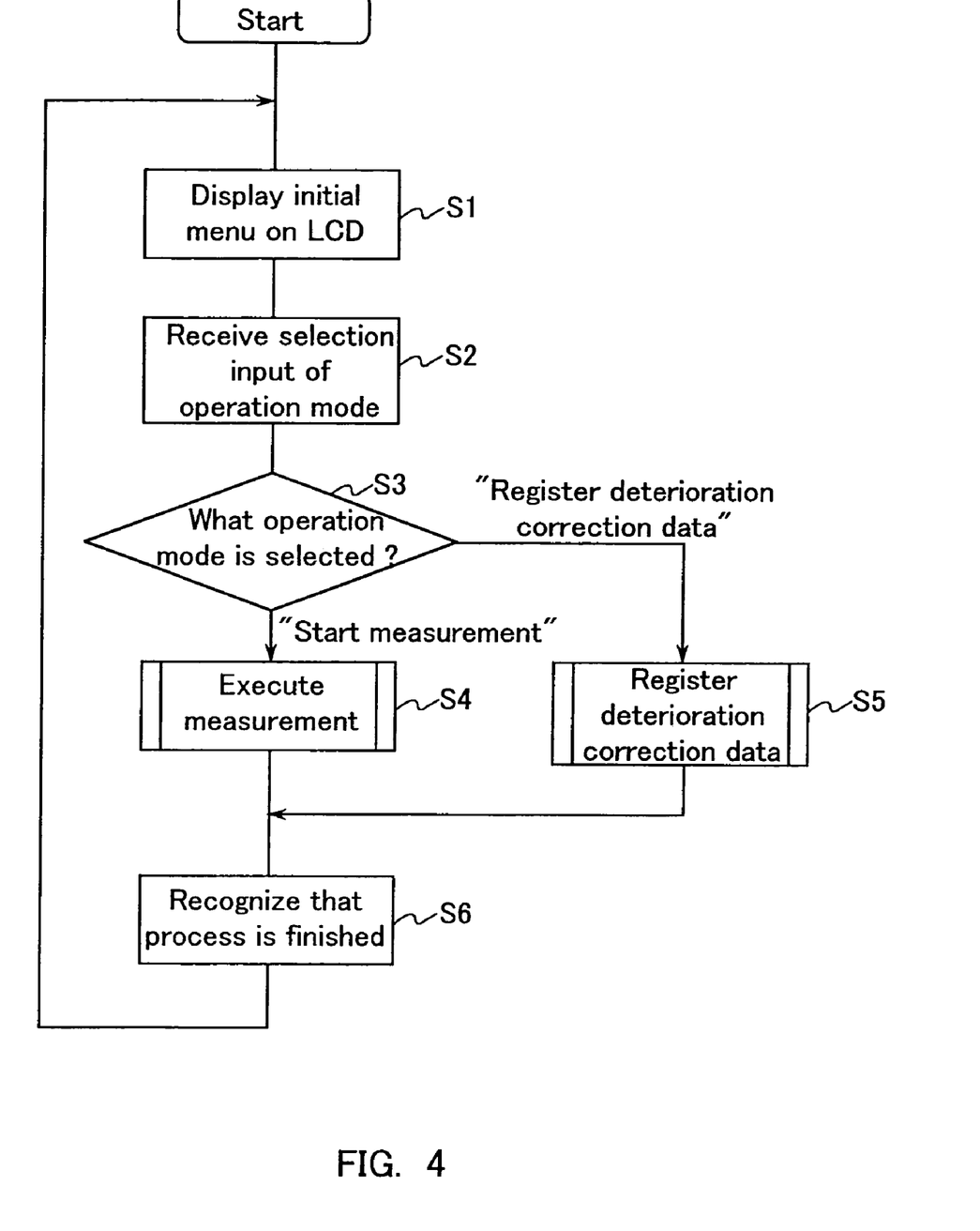
FIG. 4 is a flow chart showing procedures of a main process of the measurement instrument.

FIG. 4 is a flow chart showing procedures of a main process of the measurement instrument. The measurement instrument displays "Execute measurement" or "Register deterioration correction data," etc. as menus of options of the operation mode on an initial menu screen of the LCD display 5 (step S1).

When the operator selects/inputs the above-mentioned "Register deterioration correction data" by a sheet key 4, the CPU 1 receives this selection input (step S2) and starts the operation in the selected operation mode (step S3).

In the step S3, when the "Start measurement" is selected, the CPU 1 advances the control to the step 4, and executes the measurement using the reagent cartridge. On the other hand, when the "Register deterioration correction data" is selected in the step 3, the CPU 1 advances the control to the step S5 and carries out the process for registering the deterioration correction data about the reagent cartridge used in the measurement instrument.

When the process of the step S4 or S5 is finished, the CPU 1 outputs a message indicating that the process was finished on the LCD display 5 and the operators responds to this message and inputs a message that the message was checked by the sheet key 4. The CPU 1 receives this key entry and returns the control to the step S1 (step S6). Thus, the measurement instrument displays the initial menu on the screen of the LCD display 5 and returns to a state of waiting for an operator's input for selection. The above-mentioned steps S1 to S6 are the main process of the measurement instrument.

Herein, in the process of the step S5 of the main process, that is, in which a user of the measurement instrument uses the magnetic card attached to the purchased reagent cartridge and registers the deterioration correction data table about the reagent cartridge in the RAM 3, will be explained in detail.

As mentioned above, the reagent cartridge is shipped together with a magnetic card recording data, which are formed by a maker, representing the change over time of the reagent sensitivity for each lot. The Table below (Table 1) shows one example of data to be recorded in the magnetic card by a maker of the reagent cartridge.

As shown in Table 1, the change over time of the reagent sensitivity for each lot is recorded in the magnetic card in a form of the differential data table representing the amount of deterioration with respect to the reagent sensitivity of the previous month for every one month that has passed from the date of manufacture to the expiration date of the reagent cartridge, wherein the reagent sensitivity at the date of manufacture is made to be 100. Note here that in the example shown in Table 1, the expiration date of the reagent cartridge is 24 mounts from the date of manufacture. However, the expiration date can be set arbitrarily in accordance with the types of reagent cartridges, etc.

factured in the lot, as well as the expiration date of the reagent cartridge of the lots, etc.

Figure 5:
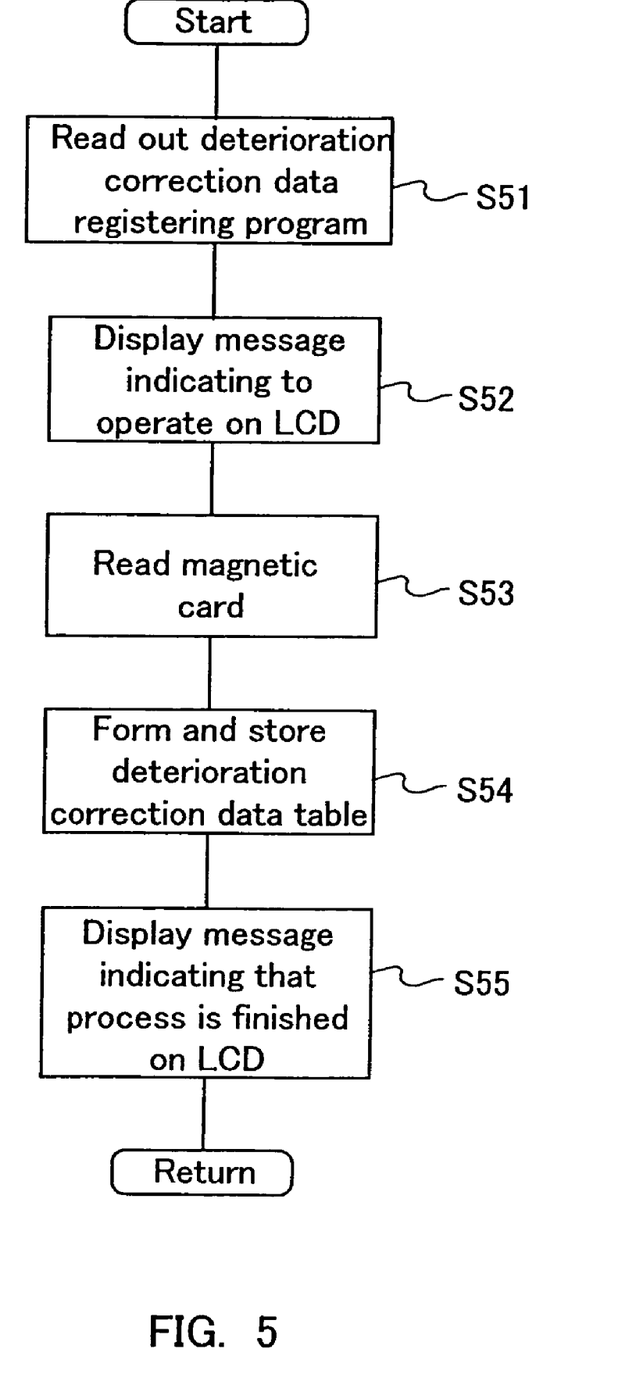
FIG. 5 is a flow chart showing detailed procedures of a deterioration correction data registering process in the step S5 of the above-mentioned main process.

The CPU 1 analyzes the information read out by the magnetic card reader 8 and allows it to be stored in a predetermined region of the RAM 3 (step S54). Note here that the CPU 1 does not record the differential data table read out by the magnetic card as it is but forms the deterioration correction data table to be stored in the RAM 3 by calculating the sensitivity $D_m$ of the reagent after m months have passed since the date of manufacture from the following expression (Formula 1) based on the differential data recorded in the differential data table. In Formula 1, m denotes the number of elapsed months from the date of manufacture, and $d_m$ denotes a differential data of this mouth in the differential data table.

$$D_m = 100 - \sum_{i=1}^{m} d_m \qquad \text{(Formula 1)}$$

TABLE 1

| A | 1 | 2 | 3 | 4 | 5 | 6 | 7 | 8 | 9 | 10 | 11 | 12 | ... | 23 | 24 |
|---|---|---|---|---|---|---|---|---|---|----|----|----|-----|----|----|
| B | 0 | 2 | 2 | 1 | 1 | 2 | 1 | 1 | 1 | 1  | 2  | 1  | ... | 1  | 0  |

A: number of elapsed months
B: differential data

Note here that in the magnetic card, together with the differential data table, information such as names of the items to be measured and item numbers corresponding to the names, number of lots corresponding to each differential data table (hereinafter, lot number will be referred to) and the date of manufacture, the number of reagent cartridge Thus, in the case where the contents of the differential data table read out by the magnetic card are, for example, the contents shown in Table 1, the contents of the deterioration correction data table stored in the RAM 3 become the contents shown in the following table (Table 2).

TABLE 2

| A | 1   | 2  | 3  | 4  | 5  | 6  | 7  | 8  | 9  | 10 | 11 | 12 | ... | 23 | 24 |
|---|-----|----|----|----|----|----|----|----|----|----|----|----|-----|----|----|
| B | 100 | 98 | 96 | 95 | 94 | 92 | 91 | 90 | 89 | 88 | 86 | 85 | ... | 81 | 81 |

A: number of elapsed months
B: reagent sensitivity manufactured in the lot, as well as the expiration date of the reagent cartridge, etc. is recorded by a maker.

FIG. 5 shows a process of step S5 in detail. Firstly, the CPU 1 reads out the deterioration correction data registering program from the ROM 2 (step S51). The CPU 1 hereafter operates in accordance with this program, and thereby a deterioration correction data registering process is executed.

Next, the CPU 1 displays a message on the LCD display 5 requesting an operator to insert the magnetic card into the magnetic card reader 8 (step S52).

When the operator inserts the magnetic card into the magnetic card reader 8 in accordance with the above-mentioned message, the magnetic card reader 8 reads out the information recorded in the magnetic card (step S53). Note here that the information read out herein includes, as mentioned above, the differential data table recorded for each lot of the reagent cartridge, the names of items to be measured and item numbers corresponding to the names, the lot number corresponding to each differential data table and the date of manufacture, the reagent cartridge number manu- Note here that a maker of a reagent cartridge may record the deterioration correction data table in a magnetic card directly without using the differential data table so that the measurement instrument registers the read out deterioration correction data table itself in the RAM 3. However, as mentioned above, it is advantageous that the configuration in which the differential data table is recorded in the magnetic card and registered in the measurement instrument when converted into the deterioration correction data table, as the volume of the information recorded in the magnetic card may be small.

Furthermore, a configuration in which differential data table read out from the magnetic card is recorded in the deterioration correction data storage unit 3b of the RAM 3 may be employed, which is advantageous in that the volume of the RAM 3 may be small. On the other hand, according to the above-mentioned configuration in which the data are converted into the deterioration correction data table and stored in the RAM 3, it is advantageous that a correction calculation after measurement can be carried out at high speed.

When the process of allowing the deterioration correction data table to be stored in the RAM 3 is finished, the CPU 1 displays a message indicating that a deterioration correction data registering process was finished on the LCD display 5 (step S55) and returns the control to the main process (Return).

As mentioned above, in the measurement instrument, by a simple operation of allowing the magnetic card reader 8 to read out the magnetic card supplied by a maker of a reagent cartridge, the deterioration correction data for each lot of the reagent cartridge can be registered in the RAM 3.

Next, the process of the step S4 of the main process of the measurement instrument, that is, the process for carrying out the measurement by using the reagent cartridge, will be explained in detail.

As mentioned above, the measurement instrument displays a screen as an initial menu on the LCD display 5 so that an operator can select the operation mode of the measurement instrument (step S1 in FIG. 5). Herein, if the operator selects "Start measurement" from the initial menu and carries out the key entry from the sheet key 4 (step S2, S3), a measurement executing process of step S4 starts.

Figure 6:
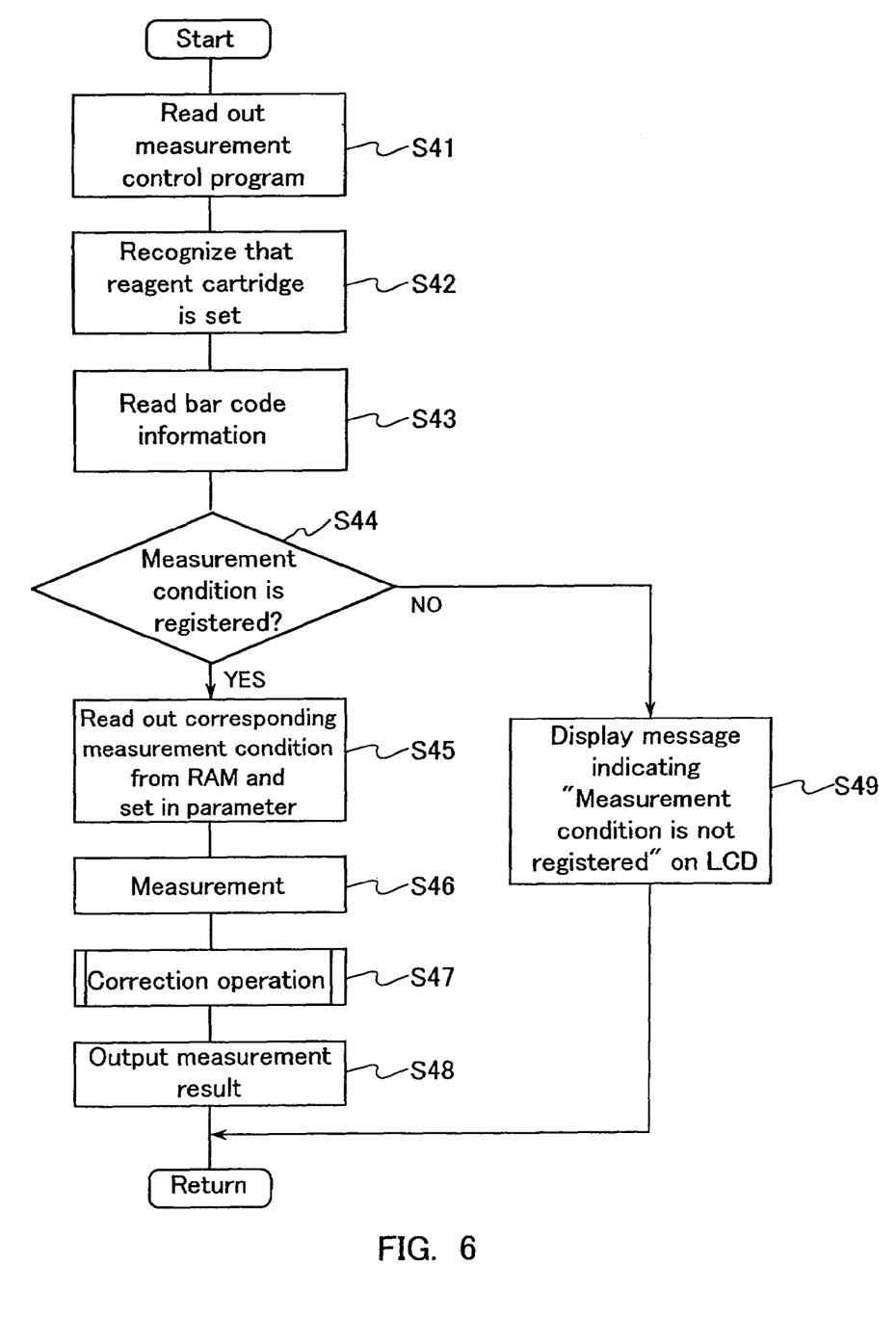
FIG. 6 is a flow chart showing detailed procedures of a measurement executing process in the step S4 of the above-mentioned main process.

As shown in FIG. 6, firstly, the CPU 1 calls the measurement control program for controlling the measurement operation from the ROM 2 (step S41). The subsequent processes can be executed as the CPU 1 operates in accordance with this measurement control program. After reading out of the program is finished, the CPU 1 displays a message indicating that the measurement starts on the LCD display 5.

In accordance with the contents displayed on the LCD display 5, an operator fills a specimen in the specimen chamber 28 of the reagent cartridge and sets the reagent cartridge in the measurement unit 11. The CPU 1 recognizes that the reagent cartridge is set in the measurement unit 11 based on ON/OFF signal of the reagent cartridge sensor mounted on the measurement unit 11 (step S42). At this time, in order to prevent misrecognition, the CPU 1 recognizes whether or not the reagent cartridge is rightly set by checking the sensor signal of the measurement unit 11 twice or more at the predetermined period.

After the CPU 1 can recognize that the reagent cartridge is set, it sends a control command to the nozzle drive unit 10 and allows the bar cord reader mounted on the nozzle drive unit 10 to read out the bar code 32 of the reagent cartridge set in the measurement unit 11 (step S43).

Then, the CPU 1 checks the bar code information read out by the bar code reader against the information stored in the RAM 3, thereby determining whether or not the measurement condition about the reagent cartridge is stored in the RAM 3 (step S44).

That is, as mentioned above, the bar code 32 of the reagent cartridge includes the information such as the names of the items to be measured, the number of the items to be measured, the lot number of the reagent cartridge, the date of manufacture, the reagent cartridge number, the expiration date, and the like, of the reagent cartridge. Therefore, the CPU 1 retrieves the measurement condition storage unit 3a of the RAM 3 by using the number of items to be measured read out by the bar code 32 as a retrieving key.

Consequently, in the case where the measurement condition including the number of the items to be measured that coincides with the retrieving key is stored in the measurement condition storage unit 3a of the RAM 3 (in the case of YES in step S44), the CPU 1 reads out the measurement condition of the item to be measured and parameter-inputs it into the measurement control program that was already read out in the step S41 (step S45).

Then, the CPU 1 displays a message indicating that the measurement operation starts on the LCD display 5 and controls the sampling pump unit 9 and the nozzle drive unit 10 in accordance with the measurement control program, thereby carrying out the measurement of the items to be measured (step S46). When the measurement is finished, a correction calculation process of the measurement results is carried out based on the deterioration correction data of the reagent cartridge stored in the deterioration correction data table of the RAM 3 (step S47) and then outputs the calculation results to the LCD display 5, a printer 6 or an input/output control unit 7 (step S48).

Then, when an operator removes the used reagent cartridge from the measurement unit 11, the CPU 1 recognizes that the reagent cartridge is removed based on the sensor signal of the measurement unit 11 and returns to the main process shown in the flow chart of FIG. 4.

On the other hand, as a result of the checking process of the step S44, in the case where the measurement conditions including the number of the items to be measured and the expiration date that coincides with the retrieving key are not stored in the measurement condition storage unit 3a of the RAM 3 (in the case of NO in step S44), the CPU 1 displays a message indicating that the set reagent cartridge is not registered on the LCD display 5 (step S49) and returns to the main process shown in the flow chart of FIG. 4.

Note here that it can be thought that the measurement conditions of the reagent cartridge are also registered in a magnetic card, etc. and supplied to a user of the measurement instrument. In this case, as in step S49, in the case where the message indicating that the measurement conditions of the reagent cartridge are not registered is displayed, a configuration may be employed, that is, as in the process for reading out the deterioration correction data table from the magnetic card and registering it in the RAM 3, a process of using the magnetic card attached to the purchased reagent cartridge, so that the measurement conditions recorded in the magnetic card are stored in the measurement condition storage unit 3a of the RAM 3 may be employed.

Herein, the correction calculation process in the step S47 will be explained in detail with reference to FIG. 7.

This correction calculating process is controlled by the deterioration correction calculating program to be called as a sub routine from the measurement control program for controlling a series of processes of steps S41 to S49 of FIG. 6. That is, after the basic calculations of the measurement and the measurement results in the step S46 shown in FIG. 6 are finished, the CPU 1 reads out the deterioration correction calculating program from the ROM 2, and takes the number of the items to be measured, the number of the reagent cartridge used for measurement, the date of manufacture and the lot number, as the parameter, from the measurement control program to the deterioration correction calculating program and starts the execution of the deterioration correction calculating program (step S471 of FIG. 7).

Next, the CPU 1 obtains the expiration date of the reagent cartridge used for measurement by retrieving the deterioration correction data storage unit 3b of the RAM 3 by using the number of the items to be measured, the number of the reagent cartridge and the lot number as a retrieving key (step S472).

The CPU 1 determines whether or not the measurement is carried out within the expiration date of the reagent cartridge based on the measurement date obtained from the clock 12 and the deterioration correction data table extracted from the step S473 (step S473). In the case where the measurement is past the expiration date (in the case of NO in step S473), the CPU 1 outputs a warning message on the LCD display 5 and the printer 6, and returns to the measurement control program (step S480).

On the other hand, in the case where the measurement date is within the expiration date (in the case of YES in step S473), the CPU 1 compares the measurement date with the date of manufacture of the lot, thereby calculating the number of elapsed days from the date of manufacture of the reagent cartridge to the measurement date (step S474).

Next, the CPU 1 retrieves the deterioration correction data storage unit 3*b* of the RAM 3 by using the number of the items to be measured, the number of a reagent cartridge and the lot number as a retrieving key, and thereby reading out the deterioration correction data table of the reagent cartridge used for measurement (step S475).

Then, the CPU 1 extracts data of two points corresponding to right before and right after the elapsed days calculated in the step S474 from the deterioration correction data table read out in the step S475 (step S476). In the case where the elapsed days from the manufacturing date to the measurement date is, for example, 2.5 months, the reagent sensitivity at the second month and the third month are extracted from the deterioration correction table as the data at two points.

The CPU 1 obtains the deterioration index calculation expression for one month between two points as a linear expression from the extracted data at two points (step S477). That is, when the data at two points extracted in the step S476 are the data of the $m_1$-th month and the $m_2$-th month ($m_1 < m_2$) and the reagent sensitivities at respective points are $D_{m1}$ and $D_{m2}$, the deterioration index calculation expression becomes as the following formula (Formula 2). Note here that in the deterioration index calculation expression, X denotes elapsed time (unit: month) from the $m_1$-th month to the measurement date, and Y denotes the reagent sensitivity at the measurement date.

$$Y = \frac{D_{m2} - D_{m1}}{m_2 - m_1} X + D_{m1} \quad \text{(Formula 2)}$$

Furthermore, the CPU 1 obtains the elapsed time from the $m_1$-th month to the measurement date and inputs it into X of the deterioration index calculation expression obtained in the step S477 and obtains the reagent sensitivity Y (step S478). In the case where the elapsed time from the manufacturing date to the measurement date is, for example, 2.5 months, 0.5 months as an elapsed time from the second month to the measurement date is input into X in the deterioration index calculation expression (Formula 2) in which $m_1$ is 2 and $m_2$ is 3 to obtain the reagent sensitivity at the measurement date. Herein, in the case of the deterioration correction data table shown in, for example, Table 2, since $D_{m1}$ is 98 and $D_{m2}$ is 96, the value of the reagent sensitivity Y on the measurement date (2.5th month from the date of manufacture) is 97 from the Formula 2.

The CPU 1 corrects the measurement data based on the reagent sensitivity Y obtained in the step S478 (step S479). That is, by multiplying 100/Y to the measurement value, the appropriate measurement value, in which the reduction of the reagent sensitivity due to the deterioration of the reagent over time is corrected, can be obtained.

Thereafter, the CPU 1 returns the measurement value after the correction to the measurement control program and at the same time returns the control (Return).

Figure 7:
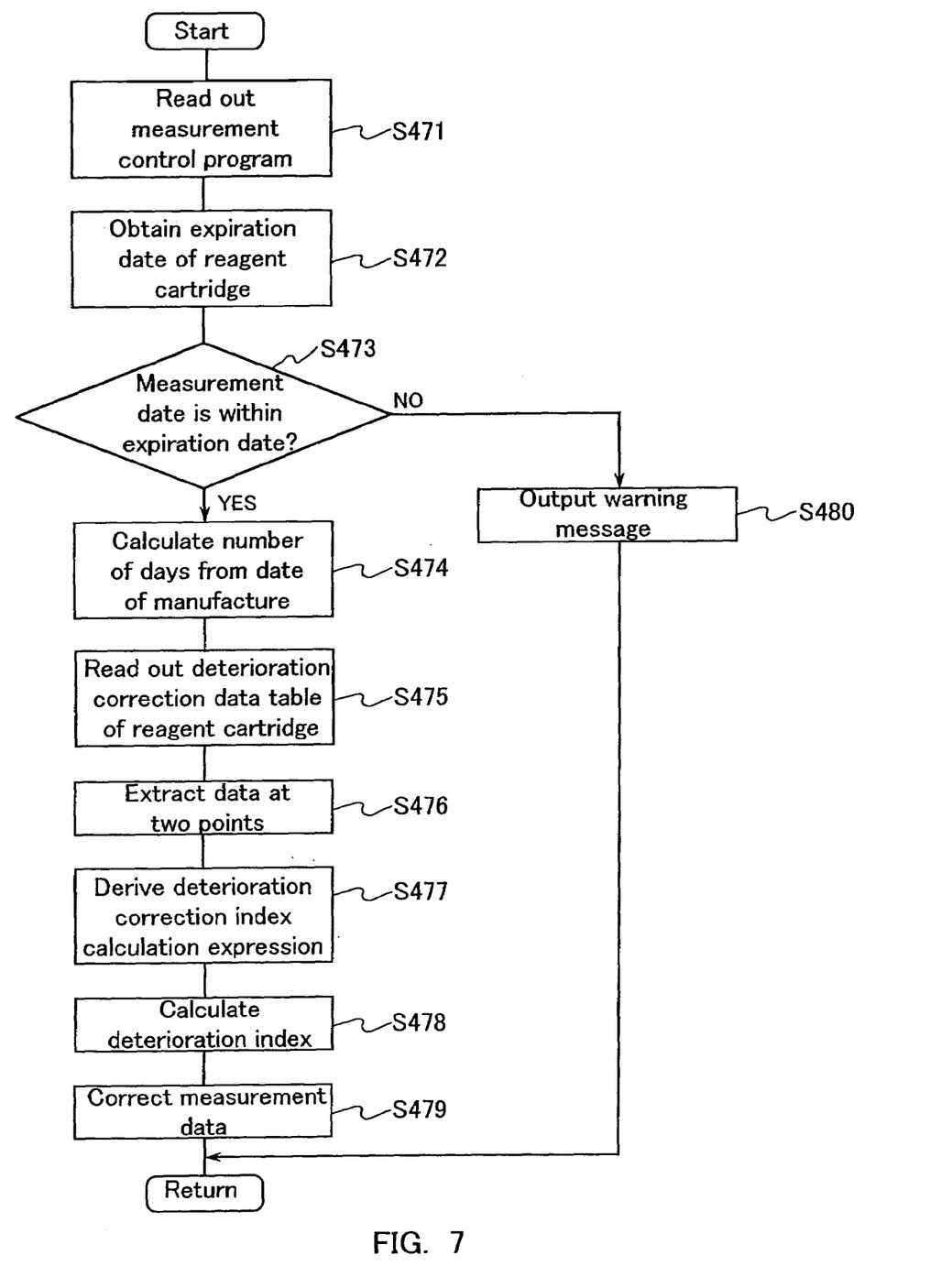
FIG. 7 is a flow chart showing detailed procedures of a correction calculation process in the step S47 of the above-mentioned measurement executing process.

As mentioned above, according to the steps S471 to S490 shown in FIG. 7, the deterioration correction calculating process of the measurement value in the step S47 in FIG. 6 can be realized.

Note here that this embodiment discloses the case where when the deterioration index calculation expression is derived in the step S477, a linear expression is obtained from two points extracted in the step S476. However, the deterioration index calculation expression is not necessarily limited to a linear expression and various kinds of interpolation expressions can be used.

Note here that the differential data table shown in Table 1 and deterioration correction data table shown in Table 2 represent the variation of the reagent sensitivity for each constant period (one month) from the date of manufacture of the reagent cartridge. The length of the time is not necessarily limited to one month and further it is not always constant intervals. For example, in the case where the reagent sensitivity changes non-linearly, etc., the deterioration correction data table may be used so that in the period in which the change of the reagent sensitivity is gentle, the interval is long (for example, two months) and in the period in which the change of the reagent sensitivity is steep, the interval is short (for example, one week). Thus, it is advantageous that more adequate correction in accordance with the deterioration of the reagent can be carried out and at the same time it is possible to use the capacity of the RAM 3 effectively.

Furthermore, as an example of the deterioration index to be recorded in the deterioration correction data table, this embodiment discloses the numerically represented reagent sensitivity for every one month that has passed with respect to the reagent sensitivity at the date of manufacture of 100. However, it is possible to use the other numeric values as the deterioration index.

Furthermore, as an example of the combination of the information indicator attached to the reagent cartridge and the indicator reading unit for reading this indicator, this embodiment shows the bar code 32 and a bar code reader of the nozzle drive unit 10. However, the combination of the information indicator and the indicator reading means is not necessarily limited to this. Any combination of an indicator that can include information concerning a cartridge (reagent information) and an instrument that can read out the information can employ an indicator recorded by an optical means or magnetic means, and other arbitrary means and a reading instrument thereof. The following are some of the other specific examples. For example, a combination of an information indicator magnetically recorded in a reagent cartridge and a means for magnetically reading out this information indicator into the nozzle drive unit 10 may be employed. Furthermore, a configuration in which printed characters are used as the information indicator and the printed characters are read out by an OCR scanner can be employed. Alternately, an IC chip is used as the information indicator, and the measurement instrument may be provided with an IC chip reader.

Furthermore, this embodiment shows an example in which information such as the lot number and the date of manufacture of the reagent cartridge directly is included in the bar code 32 of the reagent cartridge. However, the lot number and the date of manufacture may not necessarily be included directly in the bar code 32 of the reagent cartridge if the lot and date of manufacture of each reagent cartridge can be designated by comparing the other information, for example, a reagent cartridge number, etc. with the information stored in the deterioration correction data storage unit 3b of the RAM 3.

Furthermore, in the above-mentioned explanation, the example where the reagent cartridge in which the liquid reagent is filled in as the reagent carrier was explained in detail. However, as the reagent carrier, a filter paper or resin sheet, etc. which is impregnated with a reagent or a test piece formed by a reagent layer on the base material may be used.

INDUSTRIAL APPLICABILITY

As mentioned above, according to the measurement instrument of the present invention, a deterioration index representing the deterioration of a reagent over time can be calculated by interpolation based on the deterioration correction data table prepared for each lot, even in the case where the deterioration index changes non-linearly, it is possible to calculate the deterioration index at the date of the measurement exactly and at the same time, the difference between lots adequately. As a result, it is possible to provide a measurement instrument capable of obtaining the measurement data which is corrected adequately in accordance with the deterioration of the reagent over time and the difference between lots without calibration before measurement.

What is claimed is:

1. A method for correcting measurement data for carrying out a correction in accordance with a deterioration of a reagent over time with respect to the measurement data measured by using a reagent carrier that carries a reagent in accordance with items to be measured, and an information indicator, in which reagent information including information necessary to designate a lot and a date of manufacture is recorded, being attached to the reagent carrier, the method comprising:

designating a deterioration correction data table corresponding to the lot of the reagent carrier used for measurement in the deterioration correction data table containing deterioration indices showing a deterioration of a reagent over time from the date of manufacture to an expiration date at plural time points on a time series for each lot of the reagent carrier based on the reagent information obtained from the information indicator of the reagent carrier used for measurement, extracting the deterioration indices at a preceding time point and a following time point of a measurement date of the measurement data in the deterioration indices recorded in the designated deterioration correction data table, calculating a deterioration index by interpolation at the measurement date based on the deterioration indices at the preceding and following time points extracted, and carrying out a deterioration correction of the measurement data based on the calculated deterioration index.

2. The method for correcting measurement data according to claim 1, wherein the process of calculating the deterioration index by interpolation at the measurement date comprises:

deriving a deterioration index calculation expression, which satisfies the deterioration indices at the preceding time point and the following time point based on an earlier time point of the preceding time point and the following time point, calculating a number of days from the earlier time point of the preceding time and following time points to the measurement date, and substituting the number of days into the deterioration index calculation expression, thereby calculating the deterioration index at the measurement date.

3. The method for correcting measurement data according to claim 2, wherein the deterioration index calculation expression is a linear expression.

4. The method for correcting measurement data according to claim 1, wherein an information recorded medium, in which the deterioration information representing of the deterioration of a reagent over time from the date of manufacture to the expiration date for each lot is recorded, is prepared, and before measurement, the deterioration information is read from the information recorded medium, and the deterioration correction data table is formed based on the read deterioration information.

5. A program recorded medium, wherein a program for controlling the operation for carrying out deterioration correction of measurement data in accordance with a deterioration of a reagent over time, which is used for measurement in a measurement instrument for carrying out a measurement by using a reagent carrier that carries a reagent in accordance with items to be measured is recorded, and an information indicator, in which a reagent information including information necessary to designate a lot and a date of manufacture is recorded, being attached to the reagent carrier, the program comprising:

means for designating a deterioration correction data table corresponding to the lot of the reagent carrier used for measurement that refers to a deterioration correction data table storage unit storing the deterioration correction data table containing deterioration indices showing the deterioration of a reagent over time from the date of manufacture to an expiration date for each lot of the reagent carrier as the deterioration indices at plural time points on a time series based on the reagent information obtained from the information indicator of the reagent carrier used for measurement, means for extracting the deterioration indices at a preceding point and a following point of a measurement date of the measurement data in the deterioration indices contained in the designated deterioration correction data table, means for calculating the deterioration index by interpolation at the measurement date based on the deterioration indices at the the preceding and the following points extracted, and means for executing a correction calculation of the measurement data based on the calculated deterioration index.

6. The program recorded medium according to claim 5, wherein the means for calculating the deterioration index by interpolation at the measurement date comprises:

means for deriving a deterioration index calculation expression, which satisfies the deterioration indices at the preceding time point and the following time point based on an earlier time point of the preceding time point and the following time point;

means for calculating a number of days from the earlier point of the preceding time point and the following time point to the measurement date; and means for substituting the number of days into the deterioration index calculation expression, thereby calculating the deterioration index at the measurement date.

7. The program recorded medium according to claim 6, wherein the deterioration index calculation expression is a linear expression.

* * * * *